(12) United States Patent
Tagliaferri et al.

(10) Patent No.: US 10,543,378 B2
(45) Date of Patent: Jan. 28, 2020

(54) LASER SYSTEM FOR SELECTIVE TREATMENT OF ACNE

(71) Applicant: QUANTA SYSTEM S.P.A., Samarate (IT)

(72) Inventors: Marco Tagliaferri, Taino (IT); Fabio Cannone, Melzo (IT)

(73) Assignee: QUANTA SYSTEM S.P.A., Samarate (VA) (IT)

( * ) Notice: Subject to any disclaimer, the term of this patent is extended or adjusted under 35 U.S.C. 154(b) by 136 days.

(21) Appl. No.: 15/770,431

(22) PCT Filed: Oct. 27, 2016

(86) PCT No.: PCT/IB2016/056460
§ 371 (c)(1),
(2) Date: Apr. 23, 2018

(87) PCT Pub. No.: WO2017/077427
PCT Pub. Date: May 11, 2017

(65) Prior Publication Data
US 2018/0236260 A1    Aug. 23, 2018

(30) Foreign Application Priority Data

Nov. 2, 2015   (IT) .................. 102015000067842

(51) Int. Cl.
*A61N 5/06* (2006.01)
*A61B 18/20* (2006.01)
(Continued)

(52) U.S. Cl.
CPC .......... *A61N 5/0616* (2013.01); *A61B 18/203* (2013.01); *A61B 18/22* (2013.01);
(Continued)

(58) Field of Classification Search
CPC .......... A61N 5/0616; A61N 2005/0659; A61N 2005/007; A61N 2005/067;
(Continued)

(56) References Cited

U.S. PATENT DOCUMENTS 5,394,492 A    2/1995  Hwang
8,792,951 B1 *  7/2014  Mao .................... A61B 5/7221
                                                    600/340

(Continued)

FOREIGN PATENT DOCUMENTS

EP          2407807 A2      1/2012
WO     WO2008008971 A1     1/2008

*Primary Examiner* — Allen Porter
*Assistant Examiner* — Natasha Patel
(74) *Attorney, Agent, or Firm* — King & Schickli, PLLC (57) ABSTRACT

A laser system for selective treatment of acne comprising: at least two laser sources (10) having wavelength ranging from 1690 to 1750 nm which supply a first and a second laser beam respectively; a first multi-mode optical fibre (18) having a length equal to or greater than 5 m receiving said first laser beam; a second multi-mode optical fibre (18) having a length equal to or greater than 5 m receiving said second laser beam; an optical combiner (20) receiving said first and second optical fibre (18) and supplying a third laser beam to a third optical fibre (21); said third optical fibre (21) having a length equal to or greater than 5 m; said third optical fibre (21) receives said third laser beam and supplies, at its output, a fourth laser beam; a fourth optical fibre (24) which receives said fourth laser beam; a handpiece (27) associated with said fourth optical fibre (24); said fourth laser beam having a distribution intensity variance lower than or equal to 15% with respect to the mean rated value, a diameter greater than 2.5 mm, and a maximum available fluence greater than 30 J/cm2.

8 Claims, 4 Drawing Sheets

(51) Int. Cl.
    *A61B 18/22*         (2006.01)
    *A61N 5/067*        (2006.01)
    *A61B 18/00*         (2006.01)
    *A61N 5/00*          (2006.01)

(52) U.S. Cl.
    CPC ............... *A61B 2018/0047* (2013.01); *A61B 2018/00452* (2013.01); *A61B 2018/2035* (2013.01); *A61N 2005/007* (2013.01); *A61N 2005/063* (2013.01); *A61N 2005/067* (2013.01); *A61N 2005/0659* (2013.01)

(58) Field of Classification Search
    CPC ............ A61N 2005/063; A61B 18/203; A61B 2018/00452; A61B 2018/0047; A61B 2018/2035; A61B 18/22
    See application file for complete search history.

(56) References Cited

U.S. PATENT DOCUMENTS

| | | | |
|---|---|---|---|
| 2008/0267814 A1 | 10/2008 | Bornstein | |
| 2012/0120483 A1* | 5/2012 | Tagliaferri | B23K 26/046 359/356 |
| 2012/0283709 A1* | 11/2012 | Reichert | A61B 18/203 606/9 |
| 2013/0096546 A1* | 4/2013 | Mirkov | A61B 18/203 606/9 |
| 2016/0192988 A1* | 7/2016 | Albright | A61B 18/22 606/11 |

\* cited by examiner

LASER SYSTEM FOR SELECTIVE TREATMENT OF ACNE

TECHNICAL FIELD

The present invention refers to a laser system for the selective treatment of acne, and relative method.

BACKGROUND

Acne is one of the most common dermatological problems. It tends to affect males and females in adolescence, occasionally persisting into adulthood. Acne occurs mainly on the face in the form of pustules which at times leave permanent scars with undoubted psychological effects on the individual. In physiological terms, acne is to all intents and purposes a chronic skin disease with benign evolution, characterized by an inflammatory process of the hair follicle and of the appended sebaceous gland. The sebaceous gland is rich in lipidic material and is located in the derma at a depth ranging from 0.5 mm to 4 mm from the surface of the skin. The most common pharmacological treatments entail the use of benzoyl peroxide, a powerful antibacterial and keratolytic agent (i.e. able to remove the surface layers of the skin), available in the form of gel at varying concentrations which, however, can cause dermatitis. Azelaic acid has an antibacterial action and is less invasive than benzoyl peroxide but it has long reaction times, ranging from 1 to 4 months. In cases of serious acne, tretinoin is prescribed (e.g. Airol cream), or isotretinoin (Isotrex gel) and/or adapalene (Differin gel), which are synthetic derivatives of vitamin A. This can cause reddening and dryness of the skin, itching and stinging and furthermore increase sensitivity to solar radiation.

SUMMARY

To avoid the side effects of the drugs used in the treatment of acne, over the last decade the use of electromagnetic radiation emitted by appropriate light devices and/or laser sources has been developed. Pulsed laser ranging from 585 nm to 595 nm (Alster T S, McMeekin T O. Improvement of facial acne scars by the 585 nm flashlamp-pumped pulsed dye laser. J Am Acad Dermatol. 1996; 35:79-81), diode laser at 1450 nm, Erbium Glass Laser at 1540-nm (Laser Treatment of Acne Semin Plast Surg. 2007 August; 21(3): 167-174. Light/laser therapy in the treatment of acne vulgaris J Cosmet Dermatol. 2005 December; 4(4):318-20).

The laser sources or light devices proposed in the previous references operate at an incorrect wavelength for the selective treatment of acne, i.e. they emit at a wavelength at which the absorption coefficient of the lipids, found in abundance in the sebaceous gland, is lower than the absorption coefficient of water. This gives rise to an undesired effect of thermal heating of the tissue surrounding the sebaceous gland with a high risk of damaging it. In some cases a "pre-cooling" of the tissue surrounding the sebaceous gland with cryogen spray or more generally with cold liquids has been proposed ("Acne treatment with a 1.450 wavelength laser and cryogen spray cooling, Lasers in Surgery and Medicine 31:106-114 2002). Although academic studies have demonstrated the validity of this treatment, the presence of said spray considerably complicates the operation and control of the device in addition to increasing the cost thereof. It is known (U.S. Pat. No. 6,605,080 B1) that the best condition for reducing thermal damage to the tissues surrounding the sebaceous gland is for the ratio between the absorption coefficient of the lipids and the absorption coefficient of the water to be ~0.5. This condition occurs in the spectral region ranging from 1690 nm to 1750 nm. In particular at 1726 nm the absorption coefficient of the lipids is 10 $cm^{-1}$ while the absorption coefficient of the water is 5 $cm^{-1}$.

Only two studies are known in which systems able to produce laser radiation in the above-mentioned wavelength range are described. In 2006 the group of Prof. Rox R. Anderson carried out preliminary tests with a "Free Electron Laser" having wavelength at 1720 nm reaching the conclusion that the lipid absorption selective band at 1720 nm could be of interest for the selective treatment of surface targets (i.e. maximum 2 mm) like the surface sebaceous glands (Selective Photothermolysis of Lipid-Rich Tissues: A Free Electron Laser Study Lasers in Surgery and Medicine 38:913-919 2006).

In 2011 an optical fibre source was developed based on Raman scattering able to emit laser radiation at a wavelength of 1708 nm (Photothermolysis of sebaceous glands in human skin ex vivo with a 1,708 micron Raman fiber laser and contact cooling Lasers in Surgery and Medicine 43:470-480 2011) but, for the reasons discussed above, it was not optimal for the treatment of acne. Today the Raman Fiber Laser commercial sources are able to produce at the most 30 W, generally insufficient, individually, to guarantee treatment of the sebaceous glands. Due to the phenomenon of selective photothermolysis (Selective Photothermolysis: Precise Microsurgery by Selective Absorption of Pulsed Radiation, Science, 220:524-527 1983), the sebaceous gland must be reached by a dose of energy (fluence) for a time not exceeding the heat diffusion time, 0.1 sec, and such as to induce a temperature increase sufficient enough to destroy it without causing damage to the surrounding tissues. It is known (U.S. Pat. No. 6,605,080B1 and U.S. Pat. No. 7,060,061B2) that the optimal fluence value for the treatment of acne is in the range 1-50 J/cm2.

The object of the present invention is to provide a laser system for the selective treatment of acne having an emission length particularly suitable for the treatment of acne.

A further object is to provide a laser system with a flat top intensity distribution.

A further object is to provide a laser system that has a sufficient fluence for the treatment of acne.

A further object is to provide a laser system that has an extremely stable fluence in emission.

A further object is to provide a laser system that has a laser beam output having a sufficiently large diameter in order to guarantee sufficient penetration into the tissue.

According to the present invention, said objects and others are achieved by a laser system for the selective treatment of acne and a relative method according to the attached claims.

This solution offers various advantages compared to the solutions of the known art.

According to the present invention a solution has been devised which allows the production of a laser radiation:
  at the wavelength of 1726 nm, in general within the wavelength range 1690 nm-1780 nm, thus reducing the effects of heating due to absorption of the water in the tissues surrounding the sebaceous gland,
  with power >30 W thus guaranteeing an appropriate fluence for the process,
  having a beam with a flat top intensity distribution ($\eta \leq 15\%$) i.e. suitable for selective treatment of the sebaceous gland that does not induce damage in the surrounding tissues and with a diameter >3.0 mm, with extremely stable fluence in emission (fluctuations <3%) thus not altering the process depth over time, without the use of any cryogen gas which can create thermal shocks to the human skin.

BRIEF DESCRIPTION OF THE DRAWING FIGURES

The characteristics and advantages of the present invention will be evident from the following detailed disclosure of a practical embodiment thereof, illustrated by way of non-limiting example in the accompanying drawings, in which.

DETAILED DESCRIPTION OF THE INVENTION

The Applicant has realized that 50 J/cm2 can be reached with a 4.0 mm diameter spot laser, with approximately 63 W laser power, therefore more than two "Raman Fiber Laser" sources. It would be sufficient to reduce the dimension of the spot laser to obtain the fluence necessary for the process with lower power and therefore operate with a lower number of optical fibre laser sources. By way of example, a 3.5 mm spot reaches 50 J/cm2 with approximately 50 W laser power, therefore more than one source, and it is possible to obtain the fluence of 50 J/cm2 with approximately 16 W, i.e. one single "Raman Fiber Laser" source, with a spot having diameter of 2.0 mm. But, as is evident from the Monte Carlo simulations, the reduction of dimension of the spot laser diameter has the undesired effect of reducing the degree of penetration of the laser radiation into the biological tissue due to the phenomenon of scattering, thus reducing the effectiveness of the acne treatment. Consequently, considering that the sebaceous glands are at a depth ranging from 0.6 mm to 4 mm, it is desirable to have spot lasers with diameter greater than 2.5 mm in order to guarantee an effective acne treatment. In the known art (WO2008008971A1) to guarantee a certain level of penetration of the radiation into the skin, numerous relations are introduced between the wavelengths of the laser radiation and the degree of penetration of the radiation into the skin. Consequently it would be necessary to combine a plurality of laser sources at different wavelengths operating independently to avoid any undesired effects on the tissues not subject to the treatment. Consequently the use of laser sources at the more selective wavelength with a laser beam of appropriate diameter having an intensity distribution as claimed in this document appears to be an optimal solution for solving the problems of penetration of the laser radiation into the tissue. Consequently such a degree of selectivity is reached in the acne treatment process as to considerably reduce the occurrence of undesired effects such as: erythema, hypopigmentation, hyperpigmentation and edema. A further consideration is added. Allowing spacing of the laser beam on the skin, which is necessary as will be evident below, induces losses in the optical chain quantifiable at approximately 25% (4 lenses (2%)+1 fibre (8%)+sapphire window (15%)). Therefore to reach a fluence of 50 J/cm2 with a 4.0 mm spot laser, an initial laser power of approximately 85 W is required, i.e. more than two sources, which becomes 65 W in the case of a 3.5 mm spot. The conclusion is that in order to simultaneously guarantee fluence necessary for the treatment and process depth (spot laser diameter >2.5 mm), at least two "Raman Fiber Lasers" must be used. Another factor that induces a variation in the penetration level of the radiation into the tissue is the instability of the laser power. In fact, due to the process of scattering the photons in the skin, laser power fluctuations induce variations in the penetration level of the radiation into the biological tissue. It is also known that the optical fibre sources based on the phenomenon of Raman scattering emit a beam having a Gaussian intensity distribution.

Figure 2:
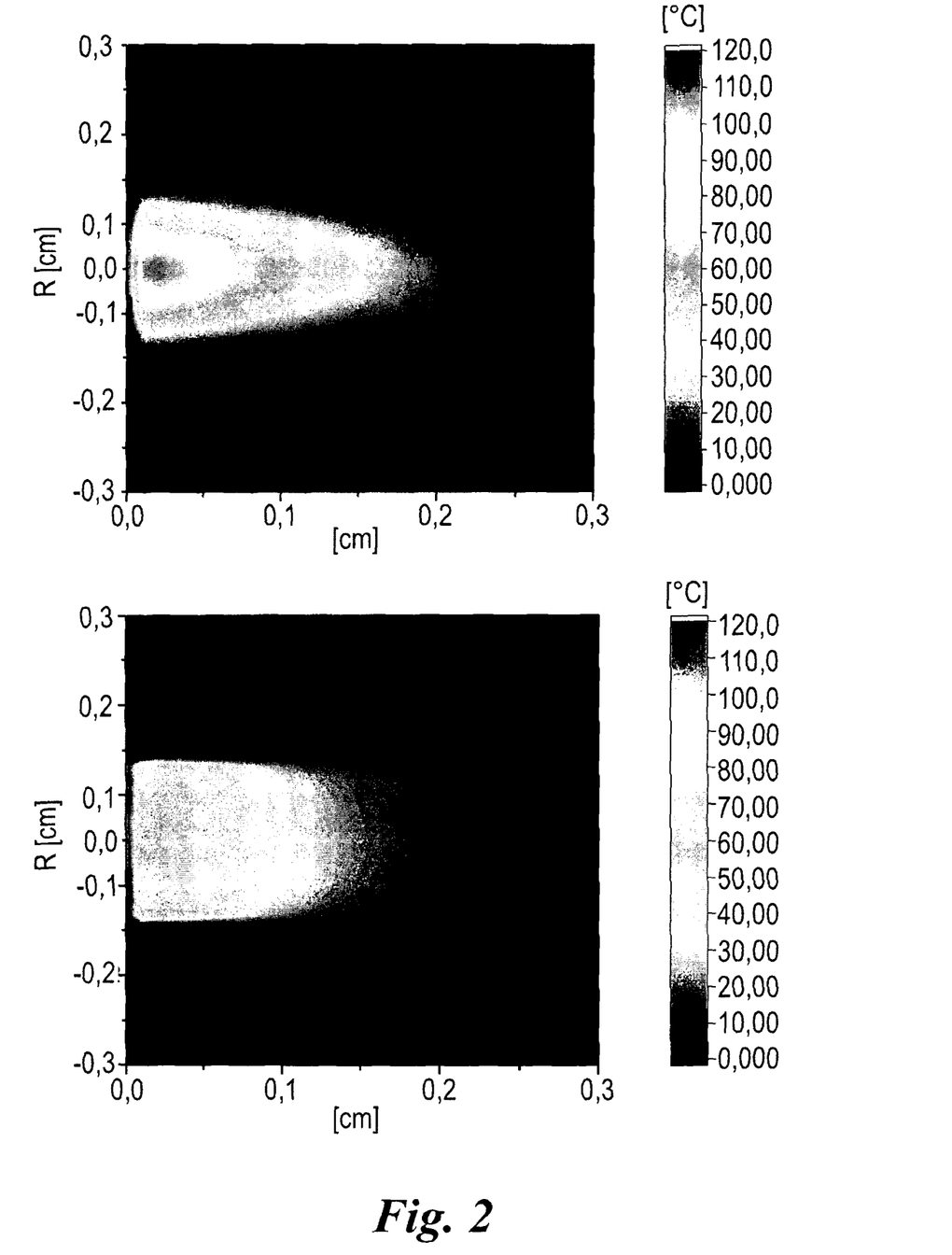
FIG. 2 shows propagation of the beam, flat top on the right and Gaussian on the left, in the biological tissue with a fluence (50 J/cm2) and diameter of 3.5 mm, where the X axis shows the depth in cm and the Y axis the dimension in cm of the beam.
Figure 3:
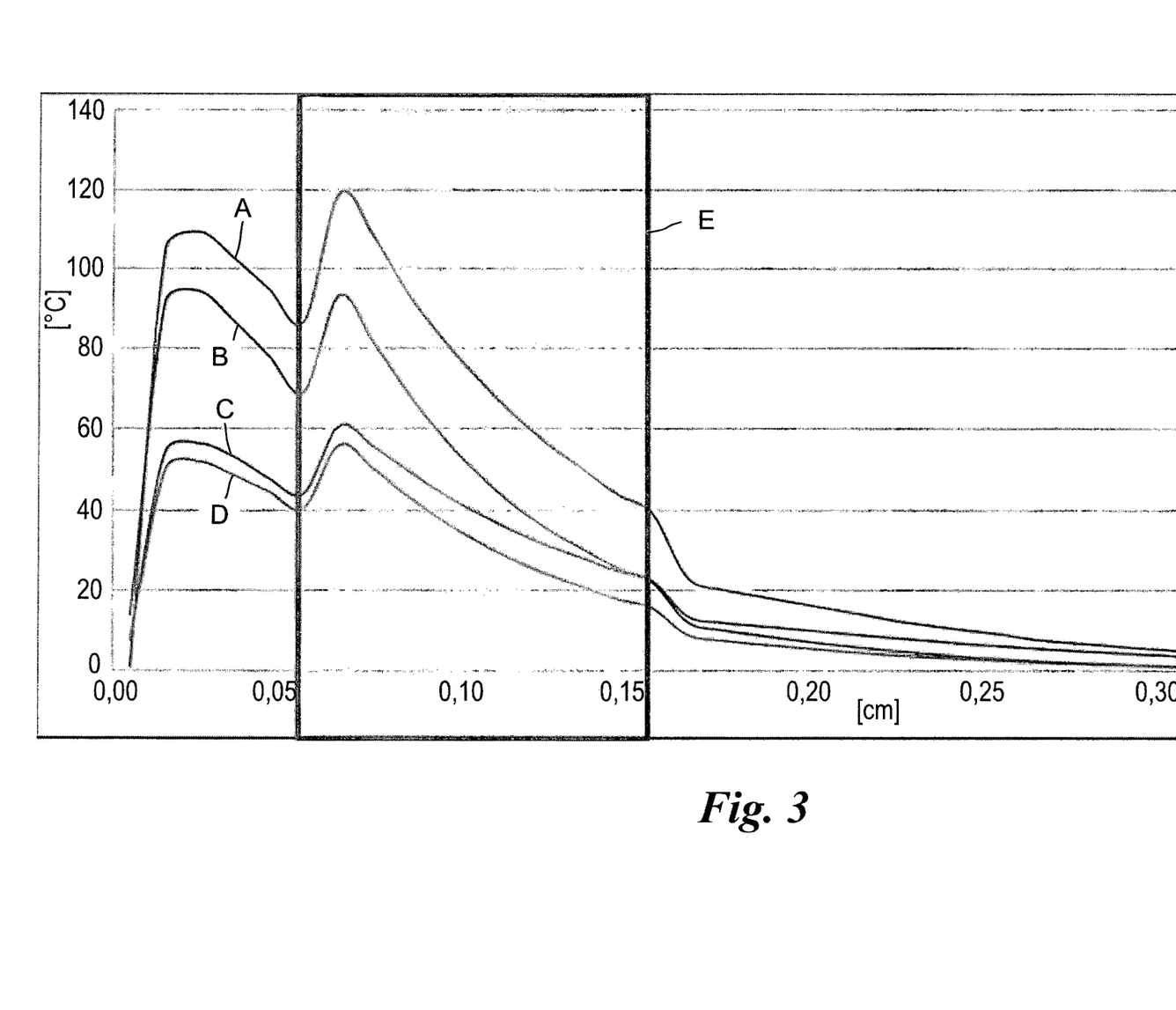
FIG. 3 shows the temperature increase induced in the tissue: with A Gaussian beam of 3.5 mm, with B flat top beam of 3.5 mm, with C Gaussian beam of 1 mm, with D flat top beam of 1 mm, where the box E highlights the position of the sebaceous gland, the X axis shows the depth in cm and the Y axis the ° C.

The Applicant has noted, by means of Monte Carlo simulations, that a laser beam at the wavelength of 1726 nm, or more generally in the wavelength range 880 nm-935 nm, 1150 nm-1230 nm, 1690 nm-1780 nm and 2250 nm-2350 nm, and having a Gaussian intensity profile striking a biological tissue like the human skin, produces a strong transfer of energy into the layers immediately adjacent to the surface of the skin, inducing considerable heating thereof (FIG. 2), thus vanifying any wavelength optimization effect. The temperature gradient that forms (FIG. 3) is such as to determine a therapeutic effect on the sebaceous gland, positioned at approximately 0.6 mm from the skin surface but, simultaneously, leads to biological damage, i.e. necrosis of the tissues located between the skin surface and the gland itself. Furthermore, experimentally, in the studies in which a beam was applied with Gaussian intensity profile, damage was observed below the sebaceous gland due to the intensity peak typical of the gradient (Gaussian) profile used (Photothermolysis of sebaceous glands in human skin ex vivo with a 1708 nm Raman fiber laser and contact cooling Lasers in Surgery and Medicine 43:470-480 2011). The same Monte Carlo simulations of the Applicant highlighted that a flat top beam, i.e. a laser beam having a high intensity distribution uniformity (intensity variance ≤15% with respect to the mean rated value), is undoubtedly the best solution for selective treatment of the sebaceous glands. In fact, the Monte Carlo simulations highlight that the thermal heating induced in the layers nearest to the skin surface by a beam having a flat top intensity profile is less than the thermal heating induced by a beam having a Gaussian profile (FIG. 2 and FIG. 3). Furthermore, the same Monte Carlo simulations indicate that the degree of penetration into the tissue by a beam having flat top distribution is approximately 20% greater than that obtained with a Gaussian profile. Here it is established that the intensity distribution is flat top when the ratio (η) between the standard deviation of the intensity (δI) with respect to the mean value of the same intensity (<I>) is lower than a pre-set value, for example 15%.

The use of a "flat top" beam is preferred in various applications (EP2407807A2, U.S. Pat. No. 5,658,275, US2008267814) and there are numerous techniques for obtaining said beam profile starting from an intensity distribution of a multi-mode source. In particular in U.S. Pat. No. 6,532,244B1 a "flat top" beam is obtained by injecting a multi-mode laser beam (V-number >2.405) into two multi-mode fibres; and on the second fibre, called spacing fibre, the fibre is bent with an appropriate radius of curvature (known as bending technique). Solutions are also known (WO2011070306A1) in which a laser beam having Gaussian intensity profile is converted by means of non-linear materials into a beam having an intensity distribution. It can be concluded that although the Raman Fiber Laser solution with emission at 1726 nm appears interesting for selective treatment of the sebaceous glands, the technological limit in terms of power on the one hand, and the emission of a Gaussian intensity profile (single mode) on the other hand, have made it so far non-applicable for the treatment of acne. Furthermore the solutions proposed in the known art to transform a beam with Gaussian distribution into a beam with "flat top" distribution are not particularly recommended. In detail, the application with introduction of the radius of curvature, in order to obtain a beam with a uniform intensity distribution, on a fibre is not advisable due to problems of power loss induced by the curvature (D. Marcuse, "Curvature loss formula for optical fibers", J. Opt. Soc. Am. 66 (3), 216 (1976)) and due to the probability of creating micro fractures in the fibres subject to curvature. Lastly the solutions that entail the use of discrete optics, such as microlenses or non-linear materials induce considerable power losses in the passage of the laser radiation through the non-linear materials.

Therefore, although the advantages of the use of an optical fibre "Raman" source (wavelength and stability in emission) are evident, the limits (low power and emission of a Gaussian intensity profile) compromise its application in the treatment of acne and the solutions present in literature (bending) are not such as to guarantee overcoming of the above-mentioned limits and obtain an appropriate level of intensity distribution uniformity functional to the selective treatment of acne.

A laser system for the selective treatment of acne, according to the present invention, comprises one or more optical fibre laser sources based on the Raman effect; the figures show three sources. By way of example, an optical fibre laser source 10 based on the Raman effect is able to emit radiation at 1726 nm, with a power in the range 30 W-35 W.

Figure 1:
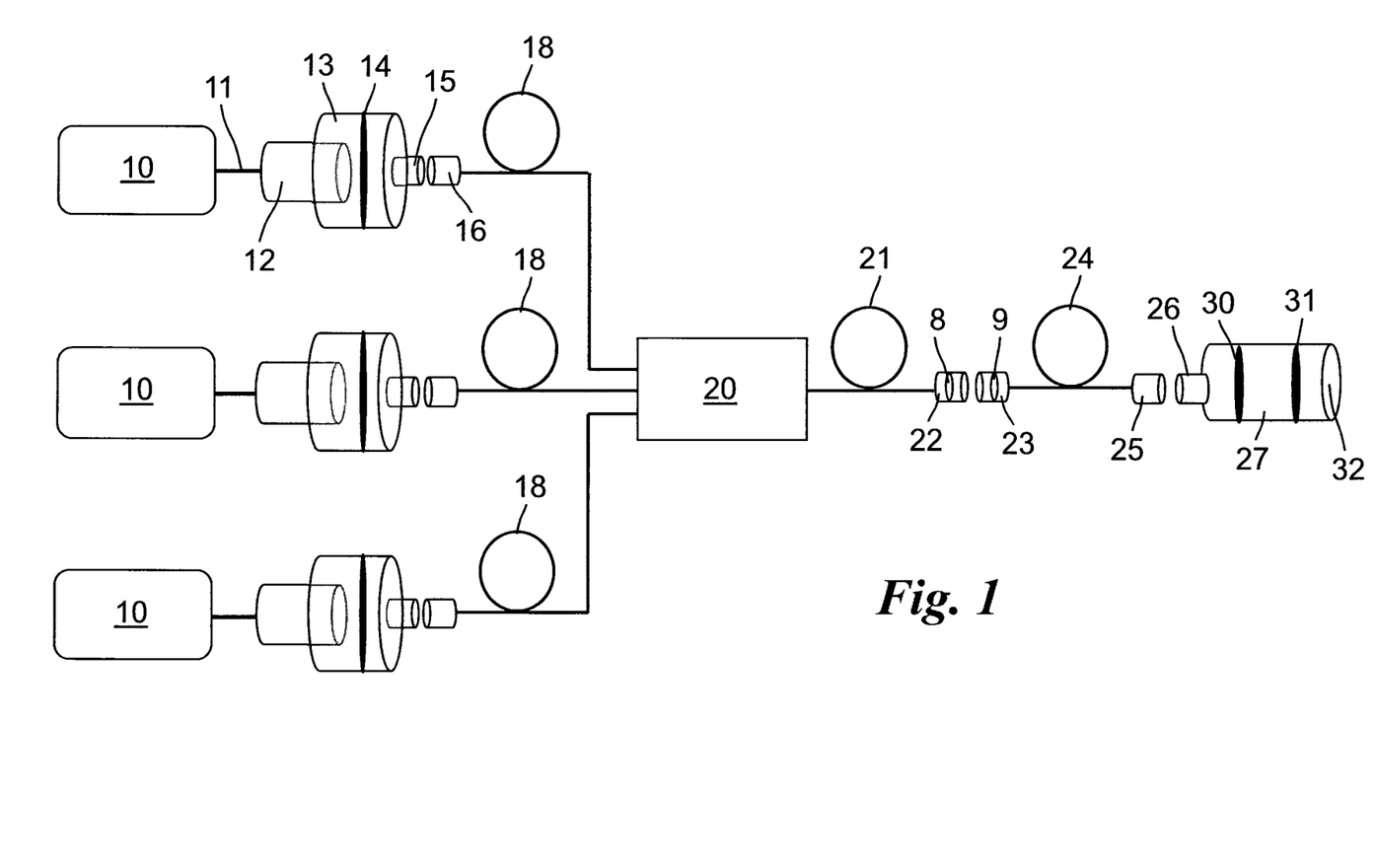
FIG. 1 shows schematically a laser system for the selective treatment of acne, according to the present invention.

Preferably, within the source 10 a red laser is inserted, or a laser with any other visible wavelength, with low power (<100 mW) at a wavelength visible to the human eye which acts as a pointer on the skin surface.

The source 10, being an optical fibre Raman source, terminates in a single mode fibre 11 having Vnumber <2.405 with a length typically of 3 metres to which an optical collimator 12 can be connected.

Figure 4:
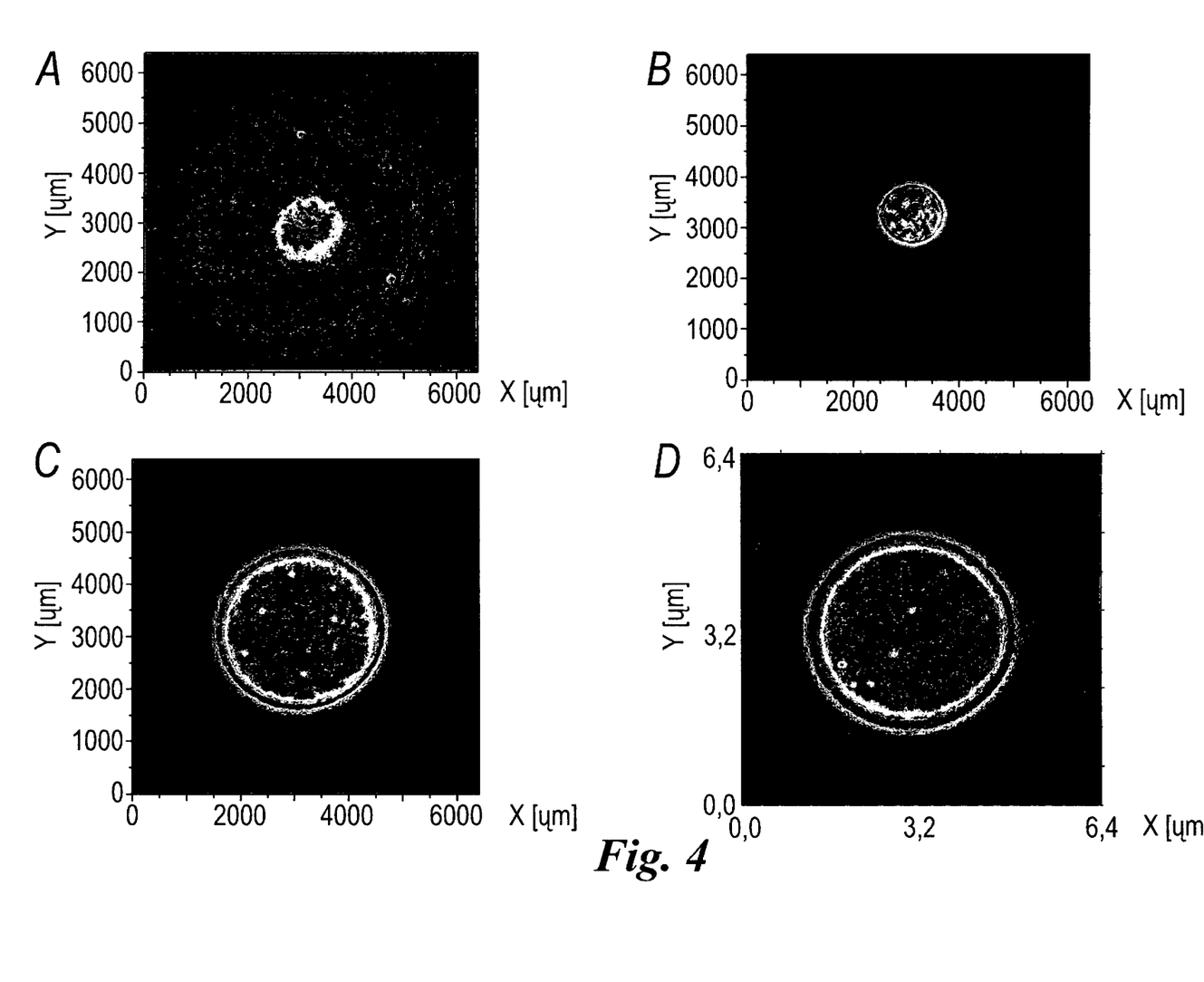
FIG. 4 shows the evolution of the intensity distribution in the layout proposed in FIG. 1 as better specified below, where the X axis and the Y axis show the dimensions of the beam (μm).

The radiation emerging from the optical collimator 12 is collimated and has a diameter in the range 3 mm-5 mm. Since the fibre 11 is a single mode fibre, the intensity profile of the radiation emerging from the collimator 12 has a Gaussian form (see FIG. 4A). The collimator 12 is optically aligned by means of an opto-mechanical interface 13 with one of the input fibres 18 of a power combiner 20 in optical fibre of the fused fibre type.

The opto-mechanical interface 13 terminates in an SMA connector 15 and the input fibre 18 begins with an SMA terminal 16.

The opto-mechanical interface 13 houses inside it a biconvex lens 14, radius of curvature R7, and effective focal length f7, chosen to maximize the coupling efficiency of the radiation emerging from the collimator 12 inside the fibre 18. The opto-mechanical interface 13 has numerous degrees of freedom both linear and angular. The input fibre 18 forms part of the optical fibre combiner 20.

As is known (US20090016681 and U.S. Pat. No. 7,272,956) an optical fibre ("pump combiner") is a passive optical fibre device which allows said output fibre 21 plus input fibres 18 to be combined in one single fibre. In the solution proposed in this patent the optical fibre combiner 20 is used to combine in the output fibre 21 the power of each of the m-sources 10. Its configuration is m×n where m is the number of the input fibres 18 while n is the number of the output fibres 21, which in our case is one. Mathematically said device can be described by means of the equation:

$$\sqrt{m} \cdot \phi_a \cdot NA_a \leq \phi_b \cdot NA_b$$

where $\phi_a$ and $\phi_b$ are the diameter of the input fibres and of the output fibre respectively and $NA_a$ and $NA_b$ are the numerical aperture of the input fibres and of the output fibre respectively. It is known that an optical fibre combiner operates to combine the power emitted by several laser sources connected to it. In the known art, there is no evidence of the fact that the combiner is used to transform a Gaussian profile beam into a "flat top" profile beam, i.e. that it acts as an intensity profile homogenizer. In the invention presented in this patent, the introduction of the fibre combiner together with the specifications of its input fibres and its output fibre is functional to obtaining this result. The input fibre is a multi-mode fibre with a Vnumber: 2.405<Vnumber≤40 and has a length of >5 metres. The output fibre is also a multi-mode fibre with a Vnumber: 2.405<Vnumber≤75 and has a length of >5 metres. It also terminates with an SMA free-standing connector 22. In the layout proposed, the two optical fibres are wound with a radius of curvature which is functional only to housing in the device. The optical fibre windings have two effects which it is desirable to avoid here. The first is power loss due to the curvature (phenomenon of "bending losses"), the second is the occurrence of micro fractures inside the curved fibre. The winding radius used in the layout proposed is greater than 3 cm. Experimental evidence has shown that said radius of curvature does not induce the above-mentioned phenomenon of "bending losses". In conclusion, the optical fibre combiner 20 which forms one single element with the fibres it is composed of 18 and 21 can be considered an "optical operator" which allows a beam with a Gaussian profile intensity distribution (FIG. 4A) to be transformed into a beam with an adequate uniform intensity distribution (FIG. 4C) and, as is known, to combine the power of several optical fibre sources. We have experimental evidence that a solution that uses only the fibres 18 and 21, without the presence of the combiner 20, provides a greater intensity distribution variance with the same length of the fibres 18 and 21. That is, if instead of the fused fibre combiner 20, the laser beams emerging from the fibres 18, having a length equal to or greater than 5 metres, were coupled in the fibre 21, having a length equal to or greater than 5 metres, by means of the collimation and focusing optics, as in the known art, a laser beam having an appropriate intensity distribution variance for the selective treatment of acne would not be obtained after the fibre 24. The known art reports the use of a "bundle of fibres" (U.S. Pat. No. 5,394,492) for combining several optical fibres in a single one. It is evident to a person skilled in the art that the method of interaction of the modes of a laser beam in a bundle structure is completely different from that occurring in a fused fibre component such as an optical combiner (20). Therefore, said solution is not applicable to our purpose since it does not guarantee the transformation of a Gaussian beam into a "flat top" beam independently of the degree of variance of the intensity distribution required. The introduction of the optical fibre combiner 20 also has the advantage of having a low laser radiation intensity loss, which does not occur when two fibres are combined with each other by means of optical components such as lenses, and does not require alignment. In conclusion, the solution proposed is based on the entirely original conception of the presence of a combiner of optical fibres, of fused type, which, in addition to the fact that its fibres have specific V-number and length parameters, acts as an optical operator able to generate a "flat top" beam with an appropriate intensity distribution uniformity without having to use possibly invasive techniques on the optical fibre known to a person skilled in the art, such as bending (EP 2407807 A2).

The SMA connector 22 of the output fibre 21 is connected to a further SMA connector 23 which terminates on one side with a spacing optical fibre 24. The spacing fibre 24 is a multi-mode fibre having a Vnumber equal or close to the Vnumber of the output fibre 21. Its nucleus can have a circular, square or rectangular profile. Its length is not a distinguishing parameter of the solution proposed. It is covered in a protective sheath so that it is not damaged. It has the sole function of transporting the laser beam onto the biological tissue and if necessary establishing the two-dimensional form of the beam profile (circular, square, etc.). The fact that it is connected to the output fibre 21 and to the handpiece 27 by means of two SMA connectors makes it an easily replaceable element, i.e. it is extremely useful in the application field in the event of failure or damage. The optical connection between the output fibre 21 and the spacing fibre 24 is provided by means of one or two lenses. In a possible configuration the beam emerging from the fibre 21 is collimated with a lens 8, with a focal length f, and then focused by the lens 9, with a focal length f, in the fibre 24. The fibre 24 is mechanically connected, for example by means of a free standing SMA connector 25, to an SMA connector 26 of a handpiece 27. The handpiece 27, which is placed in contact with the biological tissue during the treatment, allows the laser beam emerging from the fibre 24 to be further magnified. The handpiece 27 consists of an optical system adapted to provide on the sapphire window 32, which is positioned in the image plane of said system, an image of the output surface of the fibre 24 guaranteeing the same intensity distribution and a magnification of the laser beam dimensions (compare panel c and panel d of FIG. 4). In the case in point, the optical system contains two lenses 30 and 31, the ratio of which between the focal lengths determines the magnification factor M. Said magnification ratio is variable, thus obtaining different enlargements of the spot dimension. Not even this optical configuration varies the laser beam intensity distribution. To reduce the temperature of the first layers of skin, a "skin cooler" system can be possibly used positioned at the head of the handpiece 27, which by means of a Peltier cell can lower the temperature of a sapphire window 32 positioned after the lens 31. Said "skin cooler" system allows the temperature to be regulated in a range 4° C.-10° C. The sapphire window 32 more in general is an optical window chosen for its high thermal conductivity value and transparency to the radiation of interest which in any case does not alter the form of the laser beam intensity profile.

In an embodiment example of the laser system for the selective treatment of acne according to the present invention, a laser beam diameter, having Gaussian intensity distribution, of 4.5 mm (1/e2) was obtained at the output of the collimator 12 with a power of approximately 31 W at 1726 nm. The beam strikes the biconvex lens 14 which has the function of appropriately focusing the beam inside the fibre 18. The fibre 18 is a multi-mode fibre having nucleus diameter $\phi_a$=105 micron and numerical aperture $NA_a$=0.22. The fibre 18 at the input of the optical fibre combiner 20 and has a length of 11 m. In the example proposed, three (m=3) optical fibre laser sources 10, each with a power emitted of 30 W at the wavelength of 1726 nm, are combined together. Therefore the combiner 20 has a configuration 3×1 and, considering that it has a transmission efficiency greater than 96%, the power after the output 21 is greater than 86 W. The fibre 21 is a multi-mode fibre having a diameter of $\phi_b$=200 micron with a numerical aperture of $NA_b$=0.22 and length 11 m.

The lens 8 is an aspherical lens with focal length 8.18 mm, numerical aperture 0.49 and diameter 10 mm. The beam propagates towards the lens 8 with a minimum divergence (~0.073°) and is focused in the fibre 24 by the aspherical lens 9. The lens 9 has a focal length of 11.29 mm and diameter 7.2 mm.

The fibre 24 is a multi-mode fibre having nucleus diameter 200 micron, numerical aperture 0.22 and length equal to 2 m. The coupling efficiency of the radiation emerging from the fibre 21 in the fibre 24 is greater than 96%. The radiation emerging from the fibre 24 with a diameter of 200 micron and numerical aperture 0.22 with a "flat top" profile reaches the lens 30. The lens 30 is a biconvex lens having focal length of 9 mm, while the lens 31 is a convex plane lens having focal length 160 mm. In this way a spot is obtained on the biological tissue having diameter of approximately 3.5 mm. Therefore the maximum fluence available is 50 J/cm2. This is the fluence of a laser spot at the wavelength of 1726 nm having a uniform intensity profile η~5%, with respect to the mean rated value, i.e. flat top.

For the proposed purposes, a flat top laser spot is required, having diameter greater than 2.5 mm, more preferably greater than 3.0 mm, a maximum available fluence greater than 30 J/cm2, preferably greater than 40 J/cm2, and uniform intensity profile lower than 15%, preferably lower than 10%, more preferably lower than 5%. To obtain said values, it is sufficient for the length of the fibres 18 and 21 to be greater than 5 m, more preferably greater than 10 m.

The evolution of the intensity profile in the above described optical chain is shown in FIG. 4.

FIG. 4A shows the intensity distribution profile of the laser beam emerging from the collimator 12 of the optical fibre source 10.

The FIG. 4B of the figure shows the intensity distribution profile of the laser beam at the end of the fibre 18. The intensity distribution is not uniform (η=14%), in fact hot spots can be observed.

FIG. 4C of the figure shows the intensity distribution profile at the end of the fibre 21. The intensity distribution is uniform (η=5%), i.e. the beam is "flat top".

FIG. 4D of the figure shows the intensity distribution profile after the handpiece 27, i.e. after the fibre 24. The intensity distribution is identical to the one after the fibre 21.

The system described provides the power combination, and modifies the intensity distribution from Gaussian to flat top, of three sources having the same wavelength, in particular 1726 nm. The same principle can be applied also to a system which combines m sources having different wavelength. This case is particularly interesting for surgical applications which require the use, combined or alternating in time, of a wavelength to be used to produce the effect of vaporization or resection of a tissue, combined with a wavelength which provides a coagulation effect (i.e. 1920-2010 nm for vaporization and 1470-1560 nm for coagulation). A third wavelength, in the visible spectrum, could be used as pointing radiation, in particular in the red spectrum (635-655 nm) or in the green spectrum (532 nm). Furthermore said solution can be extended in general to all the wavelength ranges in which the absorption coefficient of the lipids is greater than the absorption coefficient of the water, in particular: 880 nm-935 nm, 1150 nm-1230 nm, 1690 nm-1780 nm and 2250 nm-2350 nm.

The invention claimed is:

1. Laser system for selective treatment of acne comprising:
    at least two laser sources (10) having wavelength ranging from 1690 to 1750 nm which are adapted to supply a first and a second laser beam respectively having Gaussian form, to a respective single-mode optical fibre (11);
    a first multi-mode optical fibre (18) having a length equal to or greater than 5 m adapted to receive said first laser beam;
    a second multi-mode optical fibre (18) having a length equal to or greater than 5 m adapted to receive said second laser beam;
    a fused fibre optical combiner (20) connected to said first and second optical fibre (18) and adapted to supply a third laser beam to a third optical fibre (21);
    said third optical fibre (21) having a length equal to or greater than 5 m;
    said third optical fibre (21) is connected to an output of said fused fibre optical combiner (20) and is adapted to receive said third laser beam and provides, at its output, a fourth laser beam;
    a fourth optical fibre (24) which is adapted to receive said fourth laser beam;
    a handpiece (27), comprising two lenses (30, 31), the ratio of whose focal lengths determining a magnification factor, said handpiece being associated with said fourth optical fibre (24);
    such that a laser beam output of the fourth laser beam has a distribution intensity variance lower than or equal to 15% of a mean value of radiation intensity of the fourth laser beam, a diameter greater than 2.5 mm and a maximum available fluence greater than 30 J/cm2.

2. System according to claim 1 characterised in that said first and second optical fibres (18) have a parameter V ranging from 2.405 to 40.

3. System according to claim 2 characterised in that said third optical fibre (21) has a parameter V greater than or equal to the parameter V of said first optical fibre (18).

4. System according to claim 3 characterised in that said fourth optical fibre (24) has a parameter V greater than or close to the parameter V of said third optical fibre (21).

5. System according to claim characterised in that said first optical fibre (18) has a diameter of 105 micron and numerical aperture of 0.22.

6. System according to claim characterised in that said third optical fibre (21) has a diameter of 200 micron and numerical aperture greater than or equal to 22.

7. System according to claim 1 characterised in that said handpiece (27) comprises means (30, 31) for magnifying said fourth laser beam and a sapphire window (32) positioned in an image plane of an optical system composed of the means (30) and (31).

8. Method comprising the steps of:
    Supplying a first laser beam, having wavelength ranging from 1690 to 1750 nm, to a first multi p-mode optical fibre (18) having a length equal to or greater than 5 m;
    supplying a second laser beam, having wavelength ranging from 1690 to 1750 nm, to a second multi-mode optical fibre (18) having a length equal to or greater than 5 m;
    arranging an optical combiner (20) receiving said first and second optical fibre (18); supplying a third laser beam coming out of said optical combiner (20) to a third optical fibre (21) having a length equal to or greater than 5 m;

said third optical fibre (21) supplies, at its output, a fourth laser beam;

supplying said fourth laser beam to a fourth spacing optical fibre (24); associating a handpiece (27) with said fourth optical fibre (24);

said fourth laser beam having an intensity distribution variance lower than or equal to 15% of a mean value of radiation intensity of the fourth laser beam , a diameter greater than 2.5 mm and a maximum available fluence greater than 30 J/cm2.

* * * * *